United States Patent
Nufer et al.

(10) Patent No.: US 12,408,874 B2
(45) Date of Patent: Sep. 9, 2025

(54) METHOD FOR ADJUSTING A DRIVING FORCE FOR MOVING A PATIENT TABLE OF A MAGNETIC RESONANCE APPARATUS

(71) Applicant: Siemens Healthineers AG, Forchheim (DE)

(72) Inventors: Stephan Nufer, Erlangen (DE); Julia Nufer, Erlangen (DE); Christian Hetz, Bretzfeld (DE)

(73) Assignee: Siemens Healthineers AG, Forchheim (DE)

( * ) Notice: Subject to any disclaimer, the term of this patent is extended or adjusted under 35 U.S.C. 154(b) by 175 days.

(21) Appl. No.: 18/244,434

(22) Filed: Sep. 11, 2023

(65) Prior Publication Data

US 2024/0081746 A1    Mar. 14, 2024

(30) Foreign Application Priority Data

Sep. 13, 2022 (DE) .................... 10 2022 209 524.3

(51) Int. Cl.
*A61B 5/00* (2006.01)
*G01R 33/30* (2006.01)

(52) U.S. Cl.
CPC ............ *A61B 5/704* (2013.01); *G01R 33/307* (2013.01)

(58) Field of Classification Search
CPC ....... A61B 5/704; A61B 5/318; A61B 5/6843; A61B 5/742; A61B 2560/0276; A61B 5/0077; A61B 5/1114; A61B 5/746; A61B 6/035; A61B 6/0487; A61B 5/6888; A61B 5/055; G01R 33/307; G01R 33/288
See application file for complete search history.

(56) References Cited

U.S. PATENT DOCUMENTS

| | | |
|---|---|---|
| 2017/0000446 A1 | 1/2017 | Brinker et al. |
| 2021/0093221 A1 | 4/2021 | Harder |

FOREIGN PATENT DOCUMENTS

| | | | |
|---|---|---|---|
| DE | 102012204274 A1 * | 9/2013 | ........... A61B 5/0044 |
| DE | 102015212206 A1 | 1/2017 | |
| DE | 102019214887 A1 | 4/2021 | |
| JP | H0370548 A * | 3/1991 | |
| JP | 2000245730 A | 9/2000 | |
| JP | 2006187515 A * | 7/2006 | |

OTHER PUBLICATIONS

Machine Translation of DE-102012204274-A1 (description portion only) (Year: 2013).*
Machine Translation of JP-2006-187515 (Year: 2006).*
Machine translation of JPH-0370548-A (Year: 1991).*

* cited by examiner

*Primary Examiner* — G. M. A Hyder
(74) *Attorney, Agent, or Firm* — Banner & Witcoff Ltd.

(57) ABSTRACT

In a method for adjusting a driving force for moving a patient table of a magnetic resonance apparatus, position-relevant and/or drive-relevant patient data is provided, a minimum required driving force is determined based on the provided position-relevant and/or drive-relevant patient data, the minimum required driving force for moving the patient table is determined, and the patient table is moved with the minimum required driving force.

13 Claims, 3 Drawing Sheets

METHOD FOR ADJUSTING A DRIVING FORCE FOR MOVING A PATIENT TABLE OF A MAGNETIC RESONANCE APPARATUS

CROSS REFERENCE TO RELATED APPLICATIONS

This patent application claims priority to German Patent Application No. 10 2022 209 524.3, filed Sep. 13, 2022, which is incorporated herein by reference in its entirety.

BACKGROUND

Field

The present disclosure relates to a method for adjusting a driving force for moving a patient table of a magnetic resonance apparatus. Furthermore, the present disclosure relates to a magnetic resonance apparatus which is designed so as to perform a method for adjusting a driving force for moving a patient table.

Related Art

For a magnetic resonance examination, the patient, in particular the area of the patient to be examined, is introduced into and/or positioned in a patient receiving area of a magnetic resonance apparatus, in particular in an isocenter of the magnetic resonance apparatus. For this purpose, the patient is first positioned on a patient table of the magnetic resonance apparatus and the patient table is moved into the patient receiving area together with the patient. In so doing, contact and/or a collision with the unit which is surrounding the patient receiving area can occur due to overhanging cables and/or due to protruding extremities of the patient. It is also possible for disturbances and/or dangerous situations to occur as the patient is being moved out of the patient receiving area. For example, if an arm or a hand of the patient is resting against a wall which is surrounding the patient receiving area, it is possible, due to adhesion forces for example, for the arm and/or hand to adhere to the wall which is surrounding the patient receiving area.

Such disturbances during movement of the patient table can lead to injuries to the patient and/or damage to cables and/or lines which are protruding or hanging down.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the present disclosure is to increase safety during movement of the patient table.

The disclosure is based on a method for adjusting a driving force for moving a patient table of a magnetic resonance apparatus. The method may include the following method steps:

providing position-relevant and/or drive-relevant patient data, determining a minimum required driving force in dependence upon the provided position-relevant and/or drive-relevant patient data, adjusting the minimum required driving force for moving the patient table and moving the patient table with the minimum required driving force.

In an exemplary embodiment, the magnetic resonance apparatus comprises a medical and/or diagnostic magnetic resonance apparatus which is configured and/or designed so as to acquire medical and/or diagnostic image data, in particular medical and/or diagnostic magnetic resonance image data, of a patient, in particular of the area of the patient which is to be examined. For this purpose, the magnetic resonance apparatus has a scanner unit (scanner) and a patient receiving area which is surrounded at least in part by the scanner. The patient receiving area is designed so as to receive the patient, in particular the area of the patient which is to be examined, for a magnetic resonance examination. In an exemplary embodiment, a field of view (FOV) and/or an isocenter of the magnetic resonance apparatus is arranged within the patient receiving area. In an exemplary embodiment, the FOV comprises an acquisition area of the magnetic resonance apparatus, within which the conditions for acquiring medical image data, in particular magnetic resonance image data, prevail within the patient receiving area, such as for example a homogeneous basic magnetic field. In an exemplary embodiment, the isocenter of the magnetic resonance apparatus comprises the area and/or the point within the magnetic resonance apparatus which has the optimum and/or ideal conditions for acquiring medical image data, in particular magnetic resonance image data. In particular, the isocenter comprises the most homogeneous magnetic field area within the magnetic resonance apparatus.

For positioning the patient, in particular the area of the patient which is to be examined, within the patient receiving area, the magnetic resonance apparatus has a patient positioning apparatus. The patient positioning apparatus is designed so as to position the patient for a magnetic resonance examination of the patient. In an exemplary embodiment, the patient positioning apparatus has a movable patient table which is designed so as to be able to be moved in particular within the patient receiving area of the magnetic resonance apparatus. For a magnetic resonance examination, the patient is first positioned on the patient table of the patient positioning apparatus and subsequently the patient table is moved together with the patient into the patient receiving area until the area of the patient which is to be examined is positioned within the isocenter.

In an exemplary embodiment, moving the patient table comprises moving the patient table into the patient receiving area or moving the patient table out of the patient receiving area or moving the patient table during the magnetic resonance examination within the patient receiving area. In an exemplary embodiment, the patient table is moved and/or the patient table is moved in and/or out in the longitudinal direction of the patient receiving area and/or in the longitudinal direction of the patient table. In this case, the patient table can be moved automatically, for example controlled by a controller of the magnetic resonance apparatus. In addition, the patient table can be moved, in particular moved into the patient receiving area, also only after a manual user input.

The magnetic resonance apparatus comprises in addition a drive unit (drive), for example a motor, in particular a magnetic resonance-compatible motor. A driving force for moving the patient table can be generated by means of the drive unit. In an exemplary embodiment, the patient positioning apparatus also has a controller so as to control the drive unit.

In order to move the patient table, the patient positioning apparatus, in particular the patient table, has a travel unit (traveler), for example rollers. For moving the patient table into the patient receiving area or for moving the patient table out of the patient receiving area, the magnetic resonance apparatus, in particular the scanner, has a guide rail which is arranged within the patient receiving area. In particular, the guide rail is arranged on a unit which surrounds the patient receiving area.

In an exemplary embodiment, the position-relevant patient data and/or the drive-relevant patient data comprises patient data comprising effects on a movement of the patient table and/or effects on a required driving force for moving the patient table. In particular, the position-relevant and/or drive-relevant patient data can comprise a patient size and/or a patient weight and/or an orientation and/or a positioning of the patient on the patient table and/or a distance of the area of the patient which is to be examined from the isocenter of the magnetic resonance apparatus etc. Furthermore, the position-relevant patient data and/or the drive-relevant patient data can also comprise a weight and/or a position of accessory units, which are positioned on the patient and/or on the patient table for the upcoming magnetic resonance examination, such as for example a local high frequency coil which is arranged for a magnetic resonance examination around the area of the patient which is to be examined.

In an exemplary embodiment, the position-relevant and/or drive-relevant patient data is provided by means of a provisioning unit of the magnetic resonance apparatus. In this case, the provisioning unit can comprise a registering unit for registering the patient for the upcoming magnetic resonance examination. During a registration, patient data, such as in particular a patient size and/or a patient weight and/or a positioning and/or orientation of the patient required for the upcoming magnetic resonance examination, is input by a medical operator of the magnetic resonance apparatus, in particular by means of a user interface of the magnetic resonance apparatus. Furthermore, the provisioning unit can also comprise a memory unit, wherein the position-relevant and/or drive-relevant patient data is already stored in the memory unit, for example due to preliminary examinations. Furthermore, the provisioning unit can also comprise a sensor and/or a camera, wherein the sensor and/or the camera are designed so as to acquire the position-relevant and/or drive-relevant patient data.

In the case of previous systems, adjusting a driving force involves using a maximum loading of the patient table, in particular a maximum permissible patient weight, irrespective of the actual patient weight as a basis for determining the driving force. Thus, it is also possible in dangerous situations, for example in the case of cables and/or lines hanging down, for cables and/or lines to become crushed due to the maximum driving force. In addition, it is possible when body parts become adhered to a unit which is surrounding the patient receiving area for undesirable injuries to occur to the patient due to the maximum driving force. The minimum required driving force is dimensioned in this case in such a manner that the patient table together with the patient and possibly with accessory units which are positioned on the patient table can be moved into the patient receiving area; however, in the presence of a dangerous situation and/or a disturbance, in which a greater driving force than the minimum required driving force is required for moving the patient table, the driving force is no longer sufficient for moving the patient table. In this case, the minimum required driving force may be adapted to a weight and/or a position of the patient.

The minimum required driving force at the patient table may be adjusted by means of an adjusting unit of the patient positioning apparatus. The adjusting unit may comprises the drive unit of the patient table. In addition, the adjusting unit can also be controlled by the controller of the patient positioning apparatus so as to adjust the minimum required driving force at the patient table.

The disclosure has the advantage that it is possible to provide a safe movement, in particular a safe automatic movement, of the patient table for a magnetic resonance examination. By adapting the driving force for the patient table, said driving force may be adapted to a patient weight and/or further parameters of the patient, it is possible to stop the movement of the patient table immediately in particular in a dangerous situation and/or in the presence of a disturbance, for example a body part of the patient adhering to a wall and/or unit surrounding the patient receiving area, and/or cables hanging down. It is possible in this manner to advantageously prevent injuries to the patient or damage.

In a method in accordance with the disclosure, it is possible to provide that the position-relevant and/or drive-relevant patient data may comprises at least one of the following variables:
  a weight of the patient,
  a size of the patient,
  an orientation and/or positioning of the patient on the patient table.

The position-relevant and/or drive-relevant patient data can in addition also comprise further variables, such as for example a type of an accessory unit, for example a local high frequency coil and/or an ECG unit etc., which is required for the upcoming magnetic resonance examination. In addition, the position-relevant and/or drive-relevant patient data can also comprise a weight and/or a position of the required accessory unit.

In this manner, a safe movement of the patient table can be provided and consequently risk of injury to the patient and/or risk of damage to components can be at least reduced and/or prevented.

In an exemplary embodiment of a method in accordance with the disclosure, it is possible to provide that providing the position-relevant and/or drive-relevant patient data may comprise data of a patient registration. In this case, patient data which is already available and/or has been acquired for a magnetic resonance examination can be advantageously used for adjusting the driving force for moving the patient table. The patient registration comprises a registration of the patient for a magnetic resonance examination, wherein for this purpose all the necessary patient data is acquired. The required patient data can comprise in this case a name of the patient, an age of the patient, a height of the patient, a weight of the patient, a pre-existing condition of the patient, a type of examination etc.

In an exemplary embodiment of a method in accordance with the disclosure, it is possible to provide that providing the position-relevant and/or drive-relevant patient data comprises acquiring the position-relevant and/or drive-relevant patient data by means of a camera and/or a sensor. The sensor can comprise, for example, a weight sensor for acquiring a weight of a patient and/or a touch sensor for acquiring a size and/or position of the patient. For example, the sensor can in this case be arranged in a positioning area so as to position the patient within the patient table. In an exemplary embodiment, the camera comprises a 3D camera so that in addition to a size of the patient, it is also possible to capture a perimeter of the patent and from that to determine a weight of the patient. In this manner, it is possible to provide the position-relevant and/or drive-relevant patient data in a particularly simple manner Particularly in the case of patients whose information is not available and/or with whom it is not possible to communicate during a patient registration, it is possible in this manner to provide the position-relevant and/or drive-relevant patient data in a simple and quick manner.

In an exemplary embodiment of the method in accordance with the disclosure, it is possible to provide that in a further method step during a movement of the patient table, a power required by the patient table is identified and with the aid of the identified power required by the patient table a dangerous situation during the movement of the patient table is identified. For example, it is possible by $I^2t$ monitoring to determine a power required. Dangerous situations during the movement of the patient table can comprise for example cables and/or lines which are hanging down from the patient table and which can be crushed between the patient table and the unit which is surrounding the patient receiving area. A further dangerous situation during the movement of the patient table can also be an arm of the patient adhering or becoming stuck to a wall which is surrounding the patient receiving area, such as for example after a magnetic resonance examination if a sweating arm of the patient remains adhered to the wall which is surrounding the patient receiving area. During a movement of the patient table, this can lead to the patient being injured. If such a dangerous situation is present with an obstacle and/or a disturbance during the movement of the patient table, the minimum required driving force is no longer sufficient for the movement of the patient table to continue and a greater driving force is required in order to render it possible to continue to move the patient table despite the obstacle and/or the disturbance. As a result, a current strength increases, which is apparent in the $I^2t$ progression. As a consequence, it is possible to react immediately in the presence of such a dangerous situation and consequently also advantageously to prevent undesired injuries to the patient and/or undesired damage to components. In an exemplary embodiment, the $I^2t$ progression of the patient table is evaluated by a controller of the patient positioning apparatus.

In an exemplary embodiment of the method in accordance with the disclosure, it is possible to provide that, in the presence of a dangerous situation during the movement of the patient table, a warning message is generated and output to a user. The warning message is may be generated in an automatic and/or autonomous manner, in particular by means of a controller of the patient positioning apparatus. The warning message may be output by means of a user interface of the magnetic resonance apparatus, in particular an output unit. In this case, the user interface can be arranged directly on the scanner or also within a control room. In this case, the output unit can comprise a visual output unit, such as for example a display and/or a touch display etc. and/or an acoustic output unit, such as for example a loudspeaker. The warning message can comprise in this case a visual warning message which is output by means of a display of the output unit to the user, in particular to the medical operator. As an alternative or in addition, the warning message can also comprise an acoustic warning message which is output, for example, by means of a loudspeaker of the output unit to the user, in particular to a medical operator. This embodiment of the disclosure has the advantage that, in the presence of an identified dangerous situation, a user, in particular a medical operator, is informed immediately about said dangerous situation. In addition, it is also possible in this manner for a user, in particular a medical operator, to remove and/or eliminate the dangerous situation prior to continuing the movement of the patient table and thus to contribute to a high degree of safety during the movement of the patient table during a magnetic resonance examination.

In an exemplary embodiment of the method in accordance with the disclosure, it is possible to provide that, in the presence of a dangerous situation during the movement of the patient table, the movement of the patient table is stopped immediately. In an exemplary embodiment, the movement of the patient table is stopped and/or paused in an automatic and/or autonomous manner, in particular is controlled by means of the controller of the patient positioning apparatus. It is possible in such a manner to achieve a high degree of safety during a movement of the patient table. In addition, it is possible to at least reduce and/or prevent undesired injuries and/or damage.

In an exemplary embodiment of the method in accordance with the disclosure, it is provided that a manual confirmation input is required for the movement of the patient table to be resumed. It is possible in such a manner to ensure that a user, in particular a medical operator, has been informed of the dangerous situation and has where appropriate removed and/or eliminated said dangerous situation if it is present. In addition, the manual confirmation input can be provided with a notice, in particular a danger notice, which for example advises a user, in particular a medical operator, to be particularly careful during a movement of the patient table. In an exemplary embodiment, the manual confirmation input occurs by means of a user interface of the magnetic resonance apparatus, in particular an input unit, such as for example a keyboard etc. For this purpose, an input request may be generated by a controller of the patient positioning apparatus and output to the medical operator via an output unit, for example a display.

In an exemplary embodiment of the method in accordance with the disclosure, it is possible to provide that an increased driving force is made available for the movement of the patient table to be resumed, wherein the increased driving force is determined via the required power. However, if, for example, after an automatic stop of the patient table due to a detected dangerous situation, the medical operator does not identify a dangerous situation during a check of the patient table, then the patient table can be moved with the increased driving force when the movement of the patient table is resumed. It is possible, for example, that an incorrect weight of a patient, in particular a patient weight which is too low, was acquired during the patient registration, so that the determined minimum required driving force is too low for moving the patient table. In this way, a determined driving force can be advantageously corrected. In the case of a manual actuation of the movement of the patient table, for example by turning a rotary switch and/or a jog wheel, more force can also be requested for the movement by manually turning the rotary switch and/or the jog wheel further, and in this manner a gentle movement of the patient table can take place under visual control of the user.

In an exemplary embodiment of the method according to the disclosure, it can be provided that a user output is generated, which is output to the user before time-critical magnetic resonance examinations. The user output can, for example, comprise warnings and/or a warning dialog, wherein the warnings and/or the warning dialog alert a user, in particular a medical operator, to potential dangers so that it is advantageously possible to prevent the movement of the patient table being automatically stopped during such magnetic resonance examinations. Time-critical magnetic resonance examinations could comprise, for example, magnetic resonance examinations, in which a contrast medium has been administered, and/or angiography examinations, etc.

Furthermore, the disclosure is based on a magnetic resonance apparatus which may be configured to perform a method for adjusting a driving force for moving a patient table. In an exemplary embodiment, the magnetic resonance apparatus may include:
a scanner,
a patient receiving area which is surrounded at least in part by the scanner,
a patient table for moving a patient into the patient receiving area,
a provisioning unit for providing position-relevant and/or drive-relevant patient data,
a computer unit for determining a minimum required driving force in dependence upon the provided position-relevant and/or drive-relevant patient data,
an adjusting unit for adjusting the minimum required driving force at the patient table and
a patient table travel unit for moving the patient table within the patient receiving area.

In an exemplary embodiment, the scanner of the magnetic resonance apparatus comprises a detector unit, in particular a magnet unit for acquiring the medical and/or diagnostic image data, in particular magnetic resonance image data. In this case, the scanner, in particular the magnet unit, comprises a basic magnet, a gradient coil unit and a high frequency antenna unit. In this case, the high frequency antenna unit is fixedly arranged within the scanner and is designed to output excitation pulses.

The basic magnet is designed so as to generate a homogeneous basic magnetic field having a defined magnetic field strength, such as for example having a magnetic field strength of 3 T or 1.5 T or 7 T etc. In particular, the basic magnet is designed so as to generate a strong and constant basic magnetic field. In an exemplary embodiment, the homogeneous basic magnetic field is arranged and/or located within a patient receiving area of the magnetic resonance apparatus. The gradient coil unit is designed so as to generate magnetic field gradients that are used for spatial encoding during imaging.

The computer unit for determining the minimum required driving force may have software and/or computer programs which are required for this purpose and which, when executed by a processor of the computer unit, determine the minimum required driving force in dependence upon the provided position-relevant and/or drive-relevant patient data. In this case, the controller of the patient positioning apparatus can comprise the computer unit.

As a consequence, it is possible to achieve that a safe movement, in particular a safe automatic movement, of the patient table for a magnetic resonance examination can be provided. By adjusting the driving force for the patient table, said driving force may be adapted to a patient weight and/or further parameters of a patient, an immediate stop of the movement of the patient table can be affected in particular in a dangerous situation and/or in the presence of a disturbance, for example a body part of the patient adhering to a wall and/or unit surrounding the patient receiving area, and/or cables hanging down. In this manner, it is advantageously possible to prevent injuries to the patient and/or damage.

The advantages of the magnetic resonance apparatus in accordance with the disclosure essentially correspond to the advantages of the method in accordance with the disclosure for adjusting a driving force for moving a patient table, which are described in detail above. Features, advantages or alternative embodiments mentioned herein can also be transferred to the other embodiments and vice versa.

Figure 1:
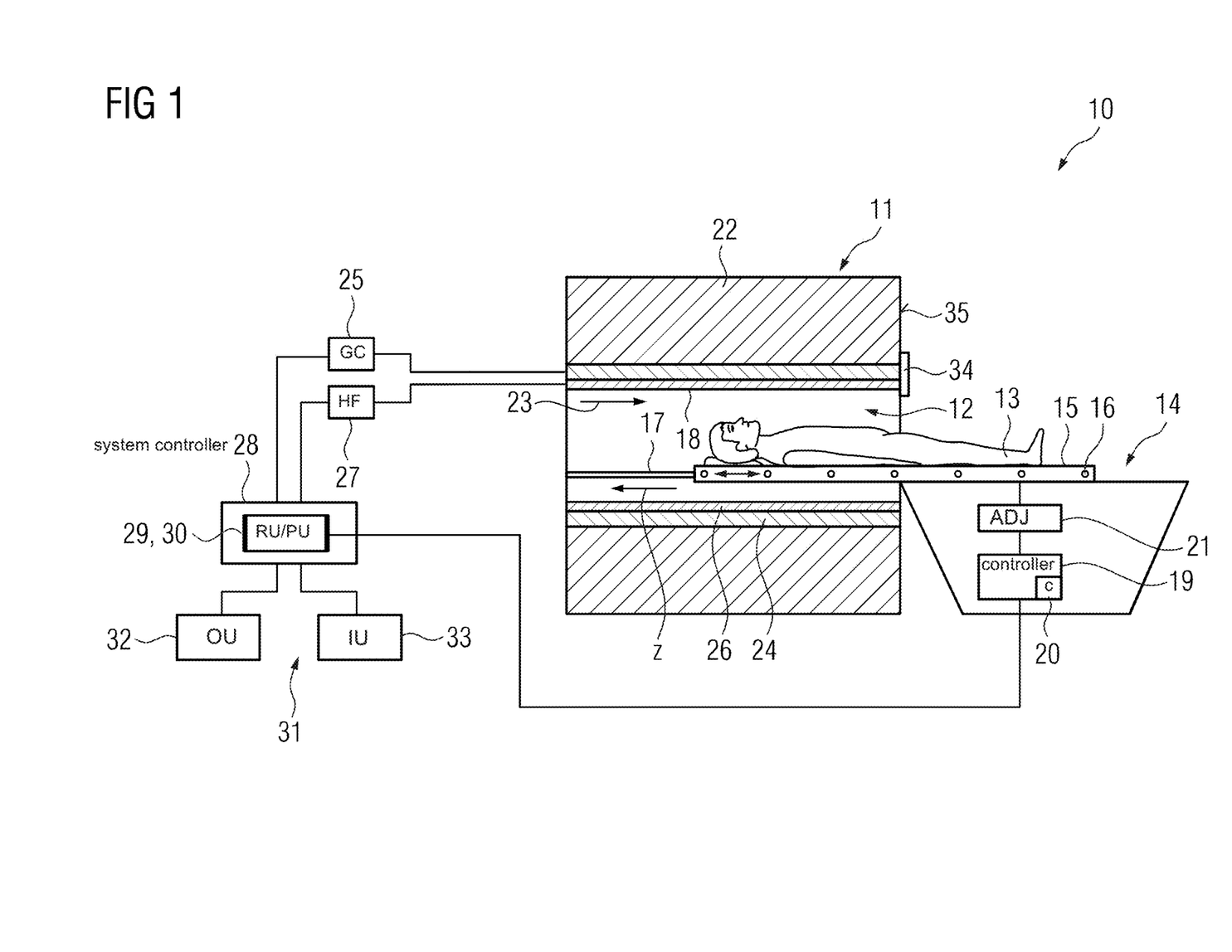
FIG. 1 shows a magnetic resonance apparatus according to an exemplary embodiment of the present disclosure.

FIG. 1 schematically illustrates a magnetic resonance apparatus 10. The magnetic resonance apparatus 10 comprises a scanner unit (scanner) 11 that is formed by a magnet unit. In addition, the magnetic resonance apparatus 10 has a patient receiving area 12 for receiving a patient 13. The patient receiving area 12 in the current exemplary embodiment is cylindrical in shape and is cylindrically surrounded in a peripheral direction by the scanner 11, in particular by the magnet unit. Fundamentally, however, a different design of the patient receiving area 12 is conceivable at any time.

The patient 13 can be pushed and/or moved by means of a patient positioning apparatus 14 of the magnetic resonance apparatus 10 into the patient receiving area 12. For this purpose, the patient positioning apparatus 14 has a patient table 15 which is configured so as to be able to be moved within the patient receiving area 12. In particular, the patient table 15 is positioned in this case in such a manner as to be able to be moved in the direction of a longitudinal extent of the patient receiving area 12 and/or in a z-direction. The patient table 15 has a travel unit 16 for this purpose. The travel unit 16 can comprise, for example, rollers which are guided on a guide rail 17, which is arranged within the patient receiving area 12. The guide rail 17 is arranged in this case on a wall 18 which is surrounding the patient receiving area 12.

Furthermore, the patient positioning apparatus 14 has a controller 19 having a computer unit (computer) 20. The computer unit 20 is designed for determining and/or calculating a driving force required for the patient table 15. In an exemplary embodiment, the computer 20 may include one or more processors configured to execute computer code to perform the operation(s) of the computer 20. The patient positioning apparatus 14 furthermore has an adjusting unit 21 which is designed for adjusting the driving force for moving the patient table 15. For this purpose, the adjusting unit (adjuster) 21 can comprise a drive unit, such as for example a motor, in particular a magnetic resonance-compatible motor. The adjusting unit 21 is controlled in this case by the controller 19 of the patient positioning apparatus 14. The adjusting unit 21, in particular the drive unit, is connected to the travel unit 16 of the patient table 15 so as to transmit the driving force. In an exemplary embodiment, the controller 19 may include processing circuitry that is configured to perform one or more functions and/or operations of the controller 19. Additionally, or alternatively, one or more components of the controller 19 may include processing circuitry that is configured to perform one or more respective functions and/or operations of the component(s).

The scanner 11, in particular the magnet unit, comprises a super-conducting basic magnet 22 for generating a strong and in particular constant basic magnetic field 23. Furthermore, the scanner 11, in particular the magnet unit, has a gradient coil unit 24 for generating magnetic field gradients which are used for spatial encoding during imaging. The gradient coil unit 24 is controlled by means of a gradient controller 25 of the magnetic resonance apparatus 10. The scanner 11, in particular the magnet unit, comprises furthermore a high frequency antenna unit 26 for exciting a polarization which is adjusted in the basic magnetic field 23 that is generated by the basic magnet 22. The high frequency antenna unit 26 is controlled by a high frequency antenna controller 27 of the magnetic resonance apparatus 10 and radiates high frequency magnetic resonance sequences into the patient receiving area 12 of the magnetic resonance apparatus 10.

In order to control the basic magnet 22, the gradient controller 25 and so as to control the high frequency antenna controller 27, the magnetic resonance apparatus 10 has a system controller 28. The system controller 28 may be configured to control the magnetic resonance apparatus 10 centrally, such as for example by performing a predetermined imaging gradient echo sequence. In addition, the system controller 28 may include an evaluation unit (not illustrated in detail; e.g., a processor) configured to evaluate medical image data that is acquired during the magnetic resonance examination. The system controller 28 has in addition a registering unit 29 which is designed so as to acquire registration data of the patient 13. In this case, the registering unit 29 is designed in addition as a provisioning unit 30 for providing position-relevant and/or drive-relevant patient data and is arranged within the system controller 28. In an exemplary embodiment, the system controller 28 may include processing circuitry that is configured to perform one or more functions and/or operations of the system controller 28. Additionally, or alternatively, one or more components (e.g., registering unit 29/101, provisioning unit 30) of the system controller 28 may include processing circuitry that is configured to perform one or more respective functions and/or operations of the component(s).

Furthermore, the magnetic resonance apparatus 10 comprises a first user interface 31, which is connected to the system controller 28. Control information, such as for example imaging parameters, and also reconstructed magnetic resonance images can be displayed for a medical operator on an output unit 32, for example on at least one monitor, of the first user interface 31. Furthermore, the first user interface 31 has an input unit 33, by means of which information and/or parameters can be input by the medical operator during a measuring procedure. The magnetic resonance apparatus 10 furthermore has a second user interface 34, which is arranged on a front side 35 of the scanner 11. The second user interface 34 likewise has an input unit and an output unit.

Figure 2:
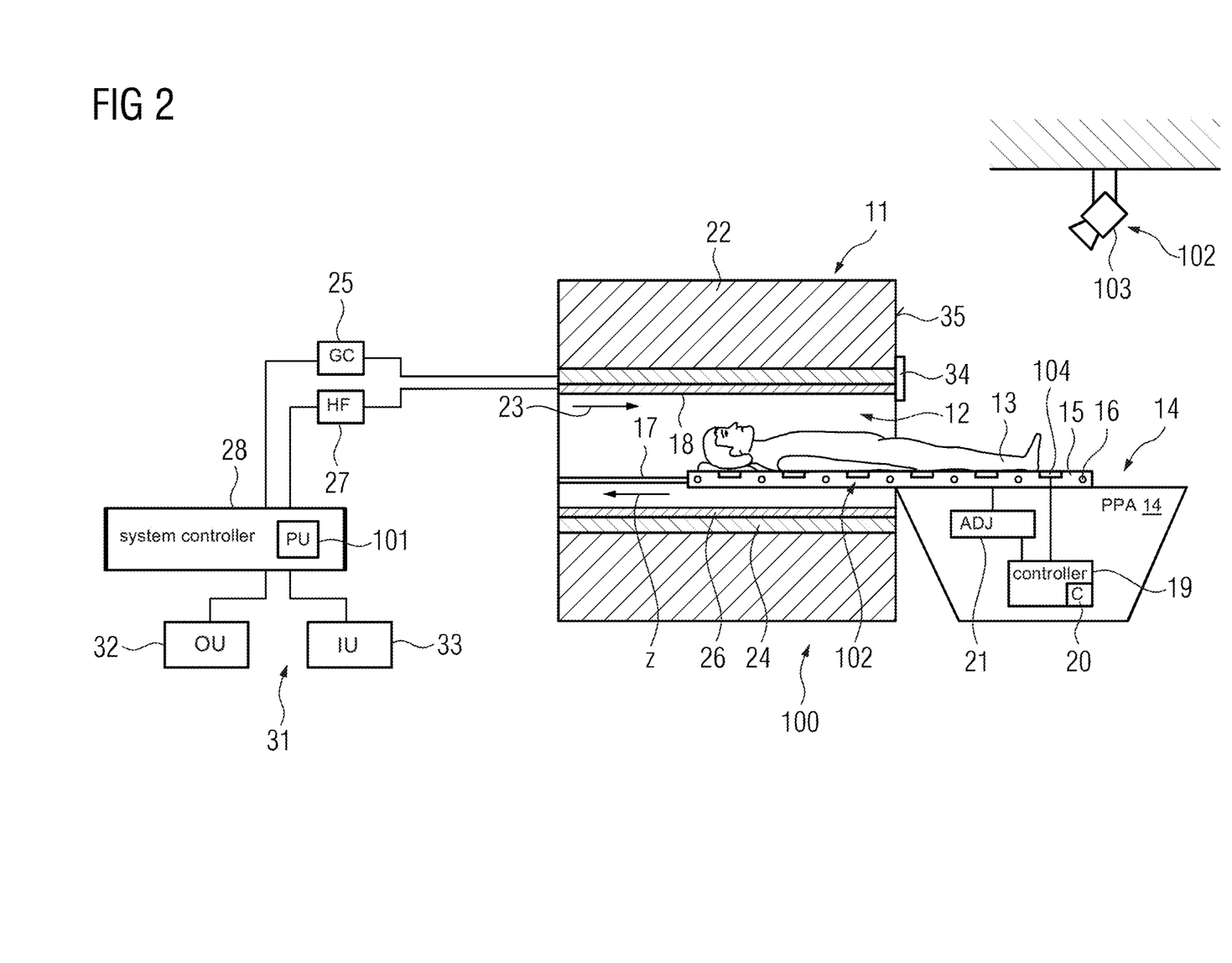
FIG. 2 shows a magnetic resonance apparatus according to an exemplary embodiment of the present disclosure.

FIG. 2 illustrates an alternative embodiment of the magnetic resonance apparatus 100. Essentially identical components, features and functions are generally numbered with the same reference characters. The following description is essentially limited to the differences to the exemplary embodiments in FIG. 1, wherein with regard to identical components, features and functions, reference is made to the description of the exemplary embodiment in FIG. 1.

The magnetic resonance apparatus 100 in FIG. 2 has a registering unit 101 and the system controller 28 comprises said registering unit. The registering unit 101 is designed for registering the patient 13 for the upcoming magnetic resonance examination. The magnetic resonance apparatus 100 furthermore has a provisioning unit 102, which in the present exemplary embodiment is designed separately from the registering unit 101. The provisioning unit 102 has in this case a camera 103 for acquiring a size of the patient 13. Furthermore, the provisioning unit 102 also has sensors 104 for acquiring a weight of the patient 13, wherein the sensors 104 are arranged within the patient table 15.

A further embodiment of the magnetic resonance apparatus 100 which is illustrated in FIG. 2 corresponds to the statements with regard to FIG. 1, to which reference is hereby made.

The magnetic resonance apparatuses 10, 100 which are illustrated in FIGS. 1 and 2 can of course comprise further components which magnetic resonance apparatuses 10, 100 usually have. A general mode of operation of magnetic resonance apparatuses 10, 100 is in addition known to the person skilled in the art and so a detailed description of the further components is omitted.

Figure 3:
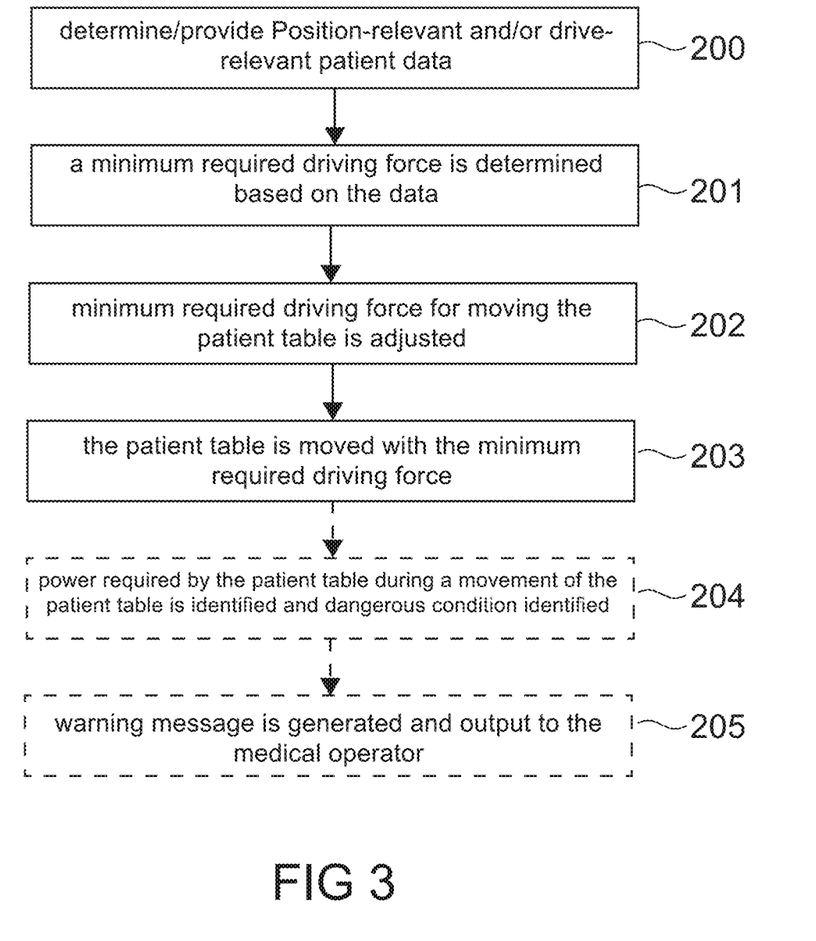
FIG. 3 shows a flowchart of a method for adjusting a driving force for moving a patient table according to an exemplary embodiment of the present disclosure.

FIG. 3 illustrates a method for adjusting a driving force for moving the patient table 15, in particular for an automatic and/or autonomous movement of the patient table 15. The method is controlled in an automatic and/or autonomous manner by the controller 19 of the patient positioning apparatus 14 which has software and/or computer programs required for this purpose. In addition, the controller 19 of the patient positioning apparatus 14 has a processor (not illustrated in detail), which is designed so as to execute the software and/or computer programs in order to perform the method for adjusting the driving force for moving the patient table 15. In an exemplary embodiment, moving the patient table 15 comprises moving the patient table 15 into the patient receiving area 12 or moving the patient table 15 within the patient receiving area 12 or moving the patient table 15 out of the patient receiving area 12.

Position-relevant and/or drive-relevant patient data is provided in a first method step 200. The position-relevant and/or drive-relevant patient data comprises in this case a weight of the patient 13 and/or a size of the patient 13 and/or an orientation and/or positioning of the patient 13 on the patient table 15. The position-relevant and/or drive-relevant patient data can in addition also comprise further variables, such as for example a type of an accessory unit, for example a local high frequency coil and/or an ECG unit etc., which is required for the upcoming magnetic resonance apparatus.

In addition, the position-relevant and/or drive-relevant patient data can also comprise a weight and/or a position of the required accessory unit.

The position-relevant and/or drive-relevant patient data may be provided by means of the provisioning unit 30, 102. The provisioning unit 30 can comprise in this case the registering unit 29, as is described in FIG. 1, wherein in this case providing the position-relevant and/or drive-relevant patient data comprises registering the patient, in particular the patient data which has been acquired when registering the patient. Alternatively, or in addition, the provisioning unit 102 can also comprise the camera 102 and/or sensors 104, as is described in FIG. 2, wherein in this case providing the position-relevant and/or drive-relevant patient data comprises acquiring the position-relevant and/or drive-relevant patient data by means of the camera 103 and/or the sensors 104.

In a second method step 201, which follows the first method step 200, a minimum required driving force is determined in dependence upon the position-relevant and/or drive-relevant patient data. Said determination is performed by means of the computer unit 20 and the controller 19 of the patient positioning apparatus 14 comprises said computer unit.

The minimum required driving force for moving the patient table 15 is adjusted in a subsequent third method step 202. The adjustment is performed by means of the adjusting unit 21.

If the upcoming magnetic resonance examination comprises a time-critical magnetic resonance examination, a user output can also be generated in this third process step 202 and output to the user, in particular to the medical operator. The user output generated in this third method step 202 can, for example, comprise a warning dialog which draws the attention of the medical operator to the dangers of the automatic and/or autonomous movement of the patient table 15 during the magnetic resonance examination, so that the medical operator can still check all possible sources of danger. The user output is generated by the controller 19 of the patient positioning apparatus 14 and output to a medical operator by means of an output unit 32 of the first user interface 31 and/or by means of the second user interface 34.

In a subsequent, fourth method step 203, the patient table 15 is moved with the minimum required driving force. The movement of the patient table 15 is controlled by the controller 19 of the patient table 15.

A power required by the patient table 15 during a movement of the patient table 15 is identified in a further optional, fifth method step 204. In addition, a dangerous situation during the movement of the patient table 15 is identified with the aid of the identified power required by the patient table 15. For example, it is possible by $I^2t$ monitoring to determine a power required by the patient table 15. Dangerous situations comprise for the most part obstacles or disturbances during the movement of the patient table 15 and can comprise for example cables and/or lines which are hanging down from the patient table 15. In addition, dangerous situations during the movement of the patient table 15 can also comprise an arm of the patient 13 adhering to a wall 18 which is surrounding the patient receiving area 12, such as for example after a magnetic resonance examination if a sweating arm of the patient remains adhered and/or stuck to the wall 18 which is surrounding the patient receiving area. If such a dangerous situation is present during the movement of the patient table 15, the minimum required driving force is no longer sufficient for the movement of the patient table 15 to continue and a greater driving force is required. As a result, a current strength increases, which is apparent in the $I^2t$ progression.

In an optional sixth method step 205 which follows the fifth process step 204, a warning message is generated and output to the medical operator in the presence of an identified dangerous situation during the movement of the patient table 15, for example by means of the output unit 32 of the first user interface 31 and/or by means of the second user interface 34. The warning message may be generated in an automatic and/or autonomous manner, in particular by means of the controller 19 of the patient positioning apparatus 14. The warning message can inform the medical operator of the dangerous situation and/or obstacles.

Furthermore, in this sixth method step 205 the movement of the patient table 15 is stopped immediately in the presence of an identified dangerous situation during the movement of the patient table 15. In an exemplary embodiment, the movement of the patient table 15 is stopped and/or the movement of the patient table 15 is paused in an automatic and/or autonomous manner, in particular by means of the controller 19 of the patient positioning apparatus 14. Furthermore, by outputting a warning message in this sixth process step 205, the medical operator can also be informed of the stopped and/or paused patient table 15.

A manual confirmation input is required in this sixth method step 205 in order for the movement of the patient table 15 to be resumed. In an exemplary embodiment, the manual confirmation input is made by means of the input unit 33 of the first user interface 31 or by means of the second user interface 34 of the magnetic resonance apparatus 10, such as for example by means of a keyboard, etc. In an exemplary embodiment, an input request is generated for this purpose by the controller 19 of the patient positioning apparatus 14 and output to the medical operator via the output unit 32 of the first user interface 31 or via the second user interface 34.

In addition, an increased driving force is provided in this sixth method step 205 for the movement of the patient table 15 to be resumed, wherein the increased driving force is determined by the computer unit 20 via the required power. Again, this can be communicated to the user via the warning message which is output at the first user interface 31 or the second user interface 34.

Although the disclosure has been further illustrated and described in detail with the aid of the preferred exemplary embodiment, the disclosure is not limited by the disclosed examples and other variations can be derived therefrom by the person skilled in the art without leaving the protective scope of the disclosure.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

The various components described herein may be referred to as "modules," "units," or "devices." Such components may be implemented via any suitable combination of hardware and/or software components as applicable and/or known to achieve their intended respective functionality. This may include mechanical and/or electrical components, processors, processing circuitry, or other suitable hardware components, in addition to or instead of those discussed herein. Such components may be configured to operate independently, or configured to execute instructions or computer programs that are stored on a suitable computer-readable medium. Regardless of the particular implementation, such modules, units, or devices, as applicable and relevant, may alternatively be referred to herein as "circuitry," "controllers," "processors," or "processing circuitry," or alternatively as noted herein.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for adjusting a driving force for moving a patient table of a magnetic resonance apparatus, the method comprising:
    determining position-relevant and/or drive-relevant patient data;
    determining, using a controller, a minimum required driving force based on the position-relevant and/or drive-relevant patient data;
    adjusting, using an adjuster, the minimum required driving force to move the patient table; and
    control, using the controller, a drive to move the patient table with the minimum required driving force.

2. The method as claimed in claim 1, wherein the position-relevant and/or drive-relevant patient data comprises:
    a weight of a patient;
    a size of the patient; and/or
    an orientation and/or positioning of the patient on the patient table.

3. The method as claimed in claim 1, wherein the position-relevant and/or drive-relevant patient data comprises data of a patient registration.

4. The method as claimed in claim 1, wherein determining the position-relevant and/or drive-relevant patient data comprises acquiring, using a camera and/or a sensor, the position-relevant and/or drive-relevant patient data.

5. The method as claimed in claim 1, further comprising:
    identifying, based on a movement of the patient table, a power required by the patient table; and
    identifying, based on the identified power required by the patient table, an occurrence of a dangerous situation during the movement of the patient table.

6. The method as claimed in claim 5, wherein, in response to the occurrence of a dangerous situation during the movement of the patient table, generating a warning message and providing the generated warning message to a user.

7. The method as claimed in claim 5, wherein, in response to the occurrence of a dangerous situation during the movement of the patient table, stopping the movement of the patient table.

8. The method as claimed in claim 7, wherein a manual confirmation input is required for the movement of the patient table to be resumed.

9. The method as claimed in claim 7, further comprising: determining, based on the required amount of power, an increased driving force for a resumed movement of the patient table.

10. The method as claimed in claim 1, further comprising generating a user output and outputting the generating the user output to the user before time-critical magnetic resonance examinations.

11. A non-transitory computer-readable storage medium with an executable program stored thereon, that when executed, instructs a processor to perform the method of claim 1.

12. A magnetic resonance apparatus comprising:
one or more processors; and
memory storing instructions that, when executed by the one or more processors, configure the apparatus to:
determine position-relevant and/or drive-relevant patient data;
determine a minimum required driving force based on the position-relevant and/or drive-relevant patient data;
adjust the minimum required driving force to move a patient table; and
control a drive to move the patient table with the minimum required driving force.

13. A magnetic resonance apparatus adapted to adjust a driving force for moving a patient table, the apparatus comprising:
a patient receiving area;
a scanner at least partially surrounding the patient receiving area;
a patient table configured to move a patient into the patient receiving area;
a provisioning unit configured to provide position-relevant and/or drive-relevant patient data;
a computer configured to determine a minimum required driving force based on the position-relevant and/or drive-relevant patient data;
an adjuster configured to adjust the minimum required driving force at the patient table; and
a patient table travel unit configured to move the patient table.

* * * * *